United States Patent
Ito et al.

(10) Patent No.: US 6,946,659 B2
(45) Date of Patent: Sep. 20, 2005

(54) APPARATUS FOR FORMING RADIATION SOURCE DISTRIBUTION IMAGE

(75) Inventors: Tadashi Ito, Kiryu (JP); Naoto Yasue, Yokohama (JP); Masao Jimbo, Otawara (JP); Hideki Ryuo, Fujisawa (JP)

(73) Assignee: Anzai Medical Kabushiki Kaisha, Tokyo (JP)

( * ) Notice: Subject to any disclaimer, the term of this patent is extended or adjusted under 35 U.S.C. 154(b) by 128 days.

(21) Appl. No.: 10/265,412

(22) Filed: Oct. 7, 2002

(65) Prior Publication Data

US 2003/0150996 A1 Aug. 14, 2003

(30) Foreign Application Priority Data

Feb. 14, 2002 (JP) ........................................ 2002-036888

(51) Int. Cl.$^7$ ................................................ G01T 1/24
(52) U.S. Cl. ............................ 250/363.06; 250/370.09; 250/370.13
(58) Field of Search ....................... 250/363.06, 370.09, 250/370.08, 363.02, 363.04

(56) References Cited

U.S. PATENT DOCUMENTS

| | | | |
|---|---|---|---|
| 3,748,470 A | | 7/1973 | Barrett |
| 4,389,633 A | * | 6/1983 | Fenimore .................... 382/204 |
| 4,435,838 A | * | 3/1984 | Gourlay ...................... 382/312 |
| 4,651,007 A | * | 3/1987 | Perusek et al. ........ 250/363.08 |
| 5,245,191 A | * | 9/1993 | Barber et al. .......... 250/363.04 |
| 5,376,796 A | * | 12/1994 | Chan et al. ............. 250/363.04 |
| 5,591,976 A | * | 1/1997 | Berthold et al. ......... 250/363.1 |
| 5,606,165 A | * | 2/1997 | Chiou et al. ............ 250/363.06 |
| 6,097,030 A | * | 8/2000 | Tokarski et al. ........ 250/363.04 |
| 6,205,195 B1 | * | 3/2001 | Lanza ......................... 376/157 |
| 6,392,235 B1 | * | 5/2002 | Barrett et al. .......... 250/363.06 |
| 6,737,652 B2 | * | 5/2004 | Lanza et al. ........... 250/363.06 |
| 2002/0145114 A1 | * | 10/2002 | Inoue et al. ............ 250/363.06 |

FOREIGN PATENT DOCUMENTS

JP 54-102085 7/1979

OTHER PUBLICATIONS

"Coded Aperture Emission CT using M–array", Transactions of the Society of Instrument and Control Engineers, vol. 28, No. 4, 426/432 (1992).

"Three–dimensional reconstruction of $^{99m}$Tc distribution by using coded aperture CT", Instrument department of the Society of Instrument and Control Engineers, 17th sensing forum (2000).

* cited by examiner

*Primary Examiner*—Albert Gagliardi
(74) *Attorney, Agent, or Firm*—Paul A. Guss

(57) ABSTRACT

A radiation source distribution image of an examinee is formed by driving X direction movement motors to move a radiation information-detecting unit in the X direction, and detecting radiation from the examinee on a stretcher placed between guide rails by using a collimator and a line sensor which constitute a detection unit.

11 Claims, 10 Drawing Sheets

APPARATUS FOR FORMING RADIATION SOURCE DISTRIBUTION IMAGE

BACKGROUND OF THE INVENTION

1. Field of the Invention

The present invention relates to an apparatus for forming a radiation source distribution image. The apparatus detects radiation from radiation sources in an examinee to form the distribution image of the radiation sources in the examinee.

2. Description of the Related Art

In nuclear medicine diagnosis, the influence of radiation exposure to an examinee should be considered. For example, when cancer is treated by the radiation to an affected part in the examinee, it is important to know the dose of the radiation to the affected part correctly. Further, it is also important to know the dose of the radiation to normal tissues around the affected part. It is also necessary to know the dose when some radiation sources are inhaled due to an accident, for example, in a nuclear power plant.

Conventionally, the dose of the radiation is estimated by simulation from the quantity of the radiation sources administered to the affected part. However, in the simulation, it is impossible to know the correct dose of the radiation.

In view of the above, for example, a gamma camera apparatus (Anger camera apparatus) has been developed, in which the gamma ray radiated from radiation sources is detected by an NaI(Tl) scintillator, and in which a distribution image of the radiation sources in the examinee is formed based on the detected information.

In the conventional gamma camera apparatus, the detector is rotated around the examinee in order to obtain a tomographic image of the examinee. Therefore, the apparatus is large, and it has been necessary to provide a dedicated bed or cot which is integrated with the apparatus into one unit.

Under these circumstances, a gamma camera apparatus with a coded aperture plate arranged in front of a scintillator has been suggested. The coded aperture plate has a large number of apertures formed in accordance with a predetermined array rule. A three-dimensional distribution image of the radiation sources in an examinee is formed based on the information obtained by the scintillator using the coded aperture plate (see "Coded Aperture Emission CT using M array", Transactions of the Society of Instrument and Control Engineers, Vol. 28, No. 4,426/432 (1992), and "Three-dimensional reconstruction of $^{99m}$Tc distribution by using coded aperture CT", Instrument department of the Society of Instrument and Control Engineers, 17th sensing forum (2000)).

When using the gamma camera apparatus with the coded aperture plate, it is possible to obtain the distribution image of the radiation sources without rotating a detector around the examinee. Therefore, it is possible to downsize the apparatus.

SUMMARY OF THE INVENTION

A general object of the present invention is to provide an apparatus for forming a radiation source distribution image which makes it possible to decrease a dedicated space by downsizing the apparatus.

A principal object of the present invention is to provide an apparatus for forming a radiation source distribution image which is compact and is accommodated in a desired space.

Another principal object of the present invention is to provide an apparatus for forming a radiation source distribution image in which it is unnecessary to provide any dedicated cot for photographing.

Still another principal object of the present invention is to provide an apparatus for forming a radiation source distribution image which makes it possible to quickly obtain a radiation source distribution image of an examinee.

Another object of the present invention is to provide an apparatus for forming a radiation source distribution image which has a simple structure.

Still another object of the present invention is to provide an apparatus for forming a radiation source distribution image which makes it possible to quickly specify the location of a radiation source in an examinee.

Still another object of the present invention is to provide an apparatus for forming a radiation source distribution image which makes it possible to obtain a detailed radiation source distribution image of an examinee.

According to the present invention, a coded aperture plate and a line sensor arranged one-dimensionally are moved along an examinee by a movable means. Accordingly, it is possible to obtain a distribution image of radiation sources. The apparatus is merely moved along the examinee. Therefore, the apparatus can be easily accommodated in a desired place when the apparatus is not operated.

Further, for example, the coded aperture plate having a plurality of apertures arranged according to an array rule of M-sequence (maximal-length sequence) is arranged between the line sensor and the examinee. Accordingly, it is possible to quickly obtain a distribution image of radiation sources in the examinee without rotating the line sensor around the examinee.

The coded aperture plate may be detachable from the line sensor. Accordingly, for example, the location of the radiation sources is quickly specified by using only the line sensor, and then a detailed distribution image of the radiation sources can be obtained for the specified area by using the coded aperture plate.

The line sensor is movable in a first direction along the examinee and in a second direction perpendicular to the first direction. Further, the line sensor can be revolved so that radiation-detecting elements are arranged in a direction perpendicular to the movement direction. Accordingly, it is possible to enhance the accuracy of the distribution image of the radiation sources in the movement direction of the line sensor.

Further, the line sensor is movable upwardly and downwardly with respect to the examinee. Accordingly, it is possible to keep a constant distance between the line sensor and the examinee. It is possible to obtain the radiation source distribution image under an identical condition of imaging irrelevant to the detected part of the examinee.

A semiconductor detection element made of CdTe or CdZnTe is used for the radiation-detecting element of the line sensor. Accordingly, it is possible to shorten the time required for measurement, and it is possible to obtain the distribution of the radiation sources highly sensitively. Further, it is also possible to identify the radiation sources based on the intensity of the detected radiation.

The distribution image of the radiation sources is formed by using the line sensor and a two-dimensional image of the examinee may be formed by using a photographing unit simultaneously for displaying these images together. Accordingly, it is possible to easily know the distribution of the radiation sources in relation to the part of the examinee.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
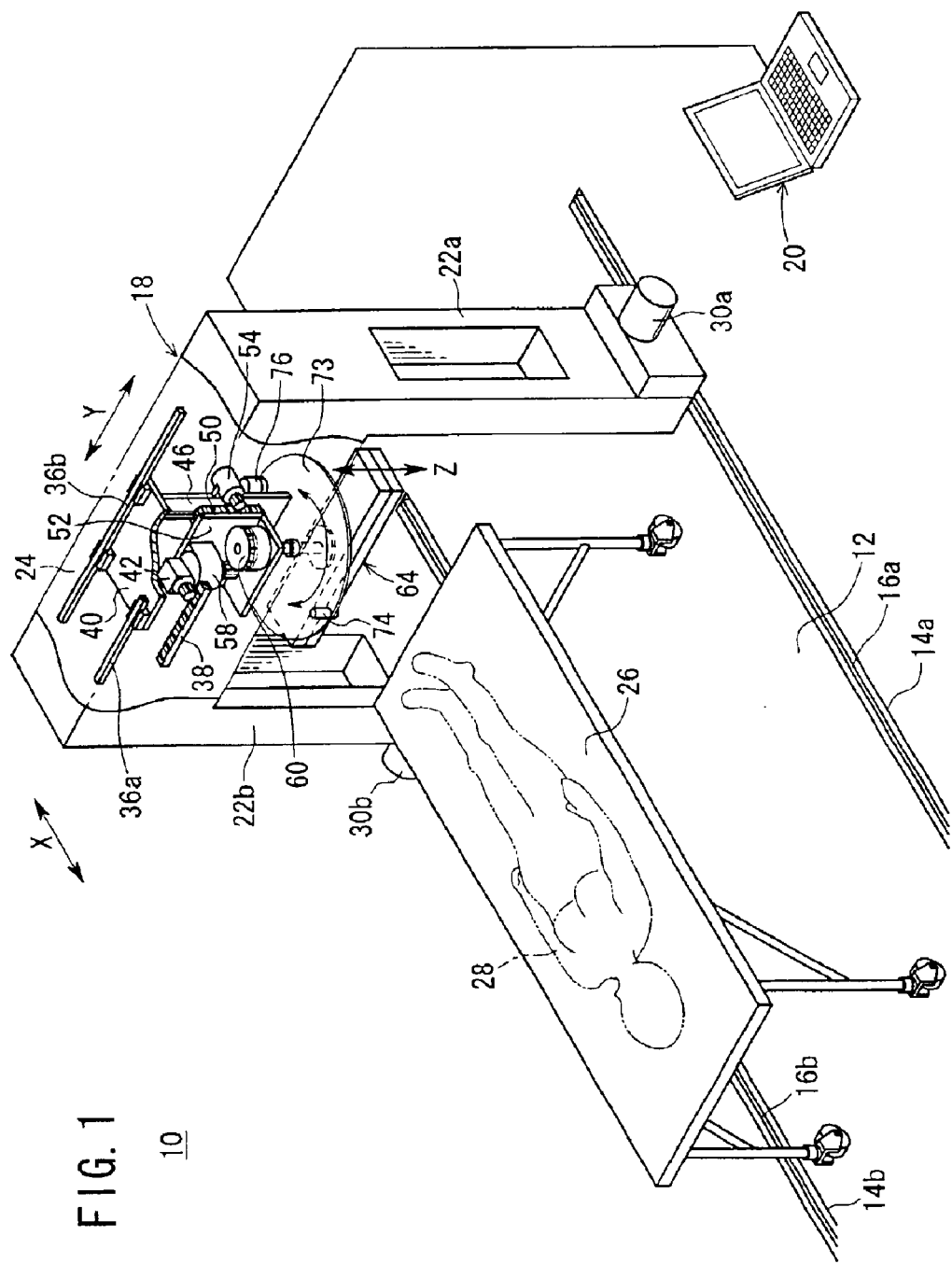
FIG. 1 is a perspective view illustrating an arrangement of an apparatus for forming a radiation source distribution image according to an embodiment of the present invention.

FIG. 1 shows an apparatus 10 for forming a radiation source distribution image according to an embodiment of the present invention. The apparatus 10 for forming a radiation source distribution image basically comprises guide rails 16a, 16b in two linear grooves 14a, 14b, respectively, laid in parallel on the floor surface 12; a radiation information-detecting unit 18 which is movable along the guide rails 16a, 16b; and an image processing unit 20 such as a personal computer which forms a radiation distribution image based on radiation information detected by the radiation information-detecting unit 18.

The radiation information-detecting unit 18 includes support pillars 22a, 22b arranged on the respective guide rails 16a, 16b, and a main body 24 by which upper ends of the support pillars 22a, 22b are bridged. In this arrangement, an examinee 28 on a stretcher 26 is placed in the space between the guide rails 16a, 16b defined by the support pillars 22a, 22b and the main body 24 (movable means).

Figure 2:
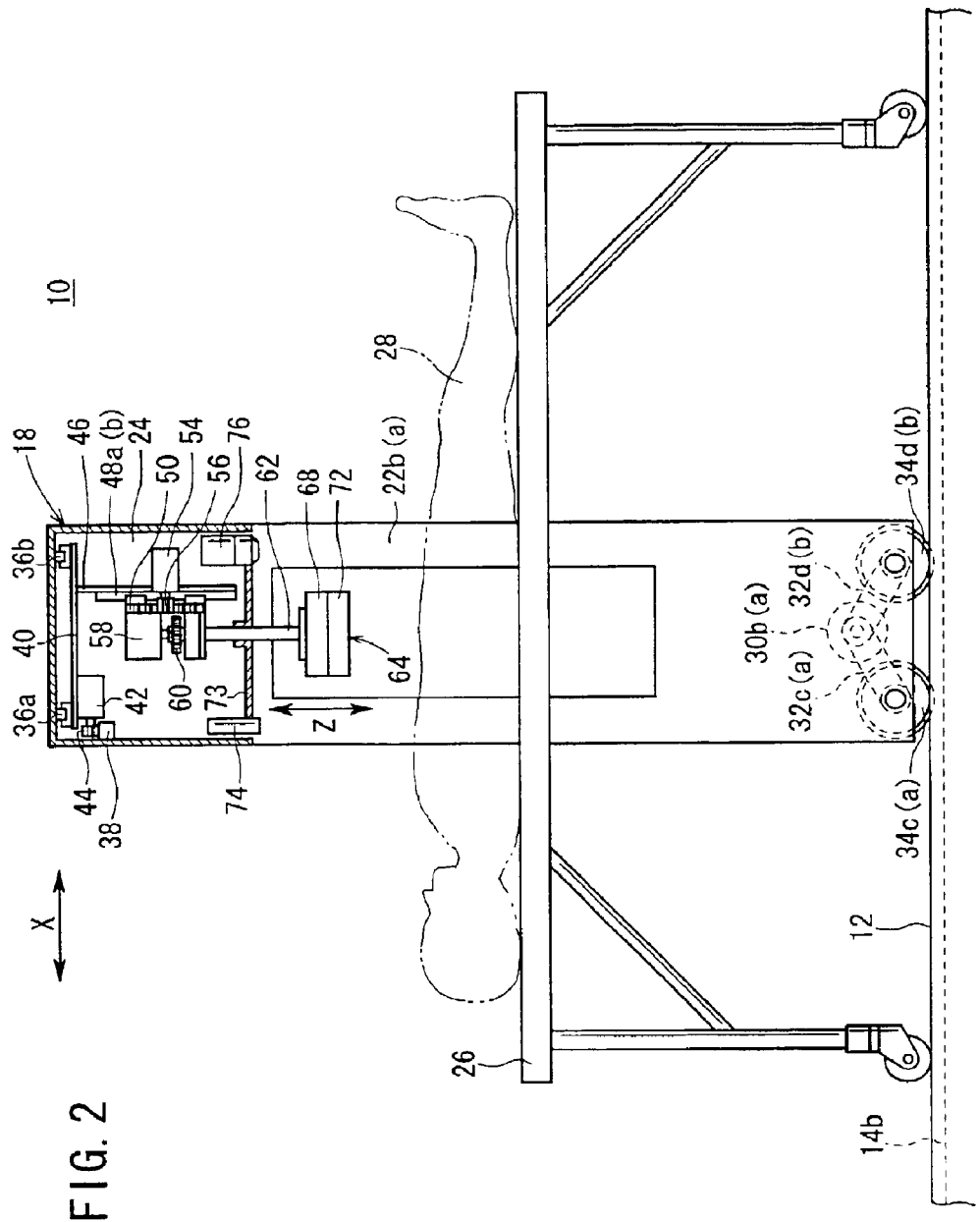
FIG. 2 is a side view illustrating the arrangement of the apparatus for forming a radiation source distribution image according to the embodiment of the present invention.
Figure 3:
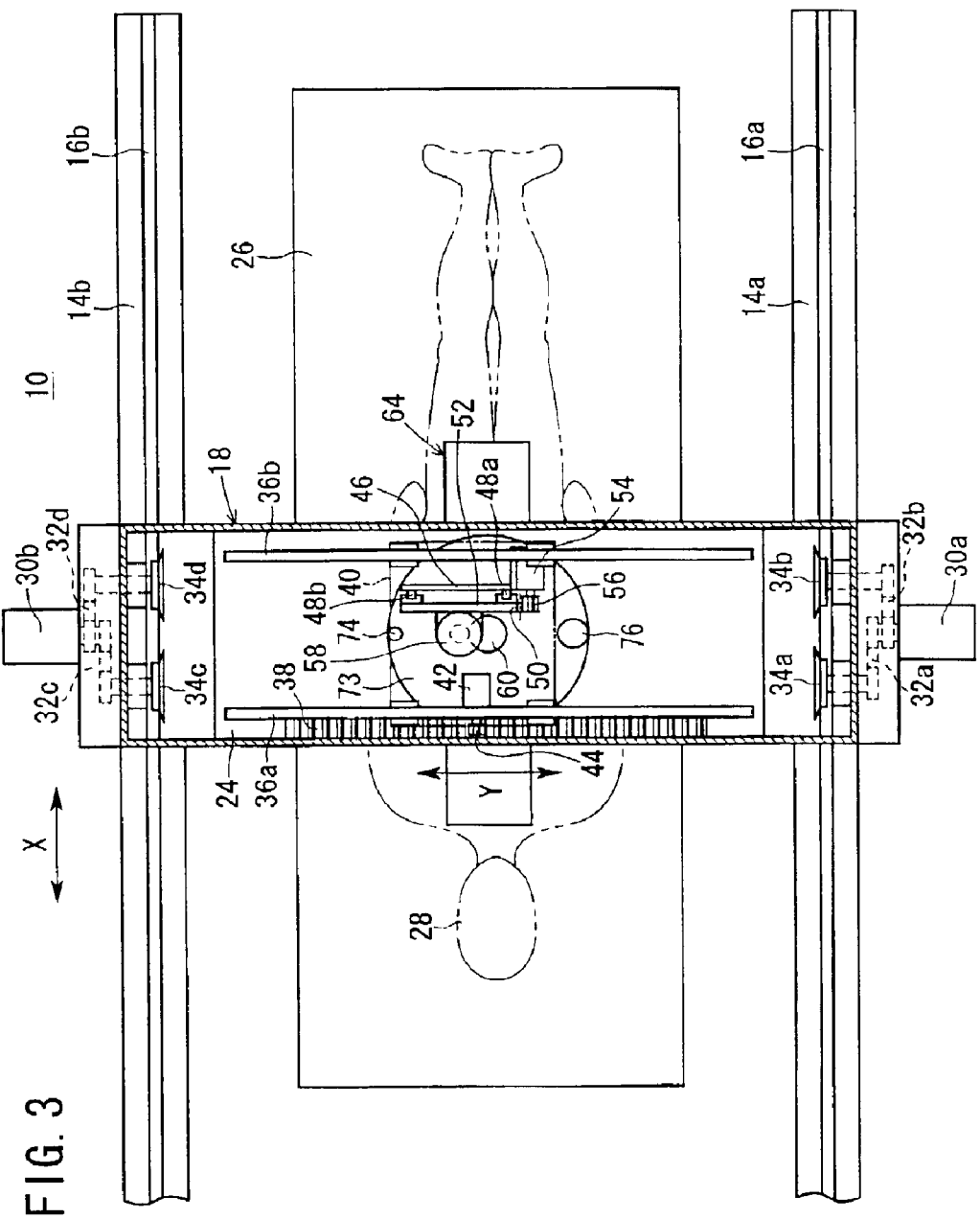
FIG. 3 is a plan view illustrating the arrangement of the apparatus for forming a radiation source distribution image according to the embodiment of the present invention.

X direction movement motors 30a, 30b for moving the radiation information-detecting unit 18 in the directions of the arrow X are arranged at the lower ends of the support pillars 22a, 22b. As shown in FIGS. 2 and 3, wheels 34a to 34d are connected to the X direction movement motors 30a, 30b by chains 32a to 32d. The wheels 34a to 34d are engaged with the guide rails 16a, 16b.

The main body 24 has guide rails 36a, 36b extending in the directions of the arrow Y shown in FIG. 3, and a rack 38 disposed in parallel to the guide rails 36a, 36b. An attachment plate 40 is guided by the guide rails 36a, 36b. A Y direction movement motor 42 is installed to the lower surface of the attachment plate 40. A pinion 44 connected to the rotary shaft of the Y direction movement motor 42 is meshed with the rack 38, and thus the attachment plate 40 is movable in the directions of the arrow Y.

As shown in FIG. 2, a bracket 46 is hung on the lower surface of the attachment plate 40. Guide rails 48a, 48b are arranged along the bracket 46, extending in the directions of the arrow Z (vertical direction). An attachment plate 52 (see FIG. 3) with a rack 50 extending in the directions of the arrow Z is guided by the guide rails 48a, 48b. A Z direction movement motor 54 is installed to the bracket 46. A pinion 56 connected to the rotary shaft of the Z direction movement motor 54 is meshed with the rack 50, and thus the attachment plate 52 is movable in the directions of the arrow Z.

A revolution motor 58 is installed to the attachment plate 52. A detection unit 64 is arranged on the lower end of a shaft 62 of a gear 60 which is meshed with the rotary shaft of the revolution motor 58.

Figure 4:
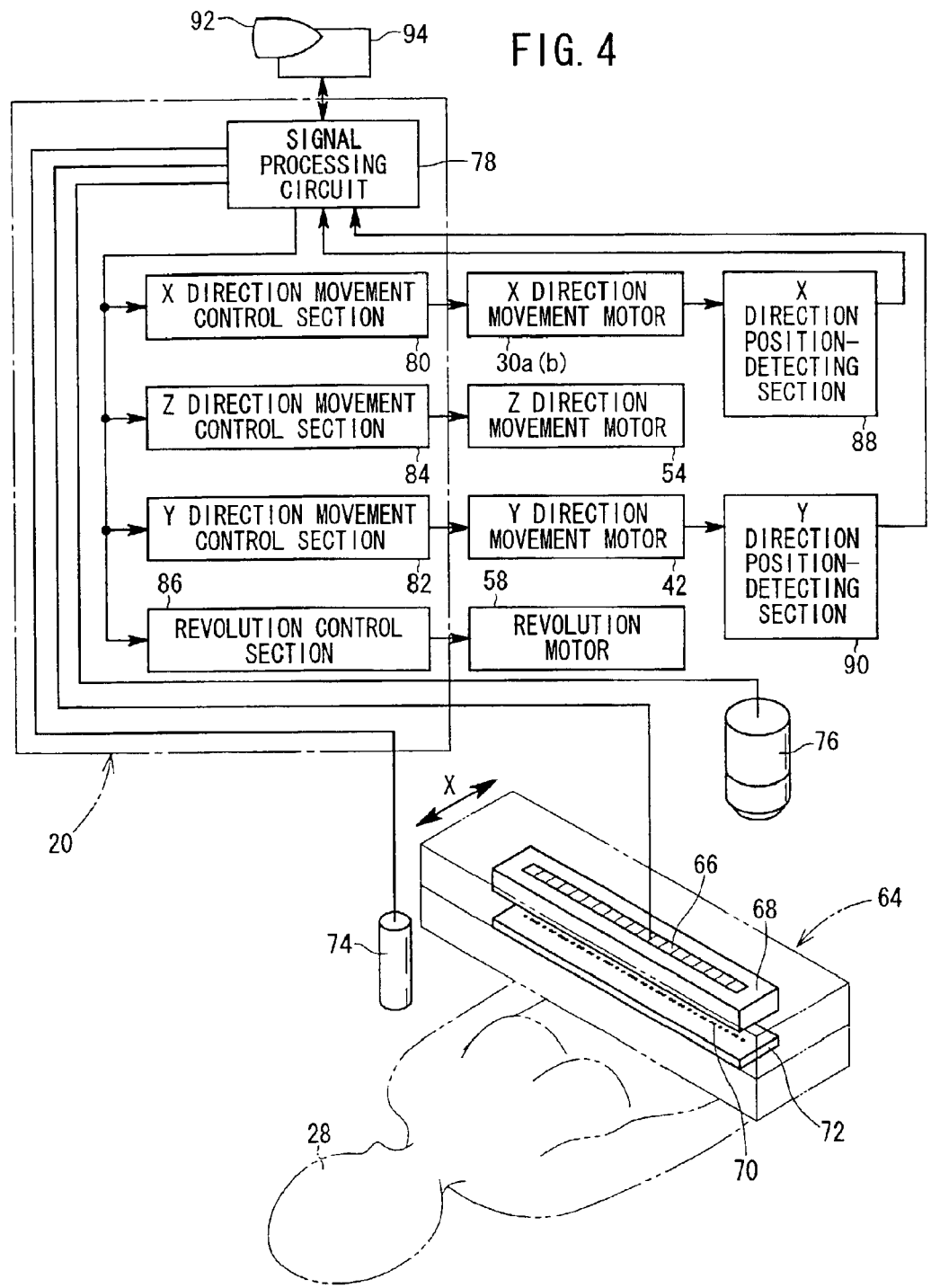
FIG. 4 shows a control block diagram centered on an image processing unit of the apparatus for forming a radiation source distribution image of the embodiment of the present invention.

As shown in FIG. 4, the detection unit 64 is provided with a line sensor 68 and a collimator 72 (coded aperture plate). The line sensor 68 includes a large number of semiconductor detection elements 66 (radiation-detecting elements) of CdTe, CdZnTe, or the like arranged one-dimensionally. The collimator 72 has a large number of apertures 70 arranged one-dimensionally along the line sensor 68 in a predetermined periodic pattern in accordance with the M-sequence or the maximal-length sequence, in which intervals of apertures 70 are based on pseudo-random sequence. In this case, the auto-correlation function of the M-sequence is close to a δ function, and the correlation function value of the M-sequence is constant other than a peak. Alternatively, the intervals of the apertures 70 can be based on the Q-sequence (quadratic residue sequence), the Gold sequence, or the Walsh code other than the M-sequence, if the sequence is the binary pseudo-random sequence.

The collimator 72 is detachable from the line sensor 68. For example, the collimator 72 may be mounted on the line sensor 68 with a magnet. Alternatively, the collimator 72 may be mounted on the line sensor 68 with a clamp member.

A disk 73 is installed to the shaft 62 which supports the detection unit 64. A distance sensor 74 and a CCD (charge coupled device) camera 76 are arranged at the outer circumference of the disk 73, and are rotatable together with the disk 73 by the shaft 62. The distance sensor 74 detects the distance between the detection unit 64 and the examinee 28. The distance sensor 74 may be an infrared sensor or the like. The CCD camera 76 photographs a two-dimensional image of the examinee 28 corresponding to the radiation source distribution image formed by the apparatus 10 for forming a radiation source distribution image.

FIG. 4 shows a control block diagram centered on the image processing unit 20 connected to the radiation information-detecting unit 18.

The image processing unit 20 has a signal processing circuit 78 (image-forming means). The signal processing circuit 78 processes the radiation detection signal supplied from the respective semiconductor detection elements 66 of the line sensor 68, the distance signal supplied from the distance sensor 74, and the image signal supplied from the CCD camera 76. Further, the signal processing circuit 78 controls the X direction movement motors 30a, 30b, the Y direction movement motor 42, the Z direction movement motor 54, and the revolution motor 58 by an X direction movement control section 80, a Y direction movement control section 82, a Z direction movement control section 84, and a revolution control section 86. An X direction position-detecting section 88 for detecting the position in the X direction of the detection unit 64 is connected to the X direction movement motors 30a, 30b. A Y direction position-detecting section 90 for detecting the position in the Y direction of the detection unit 64 is connected to the Y direction movement motor 42. The signal processing circuit 78 is connected with a display unit 92 (display means) for displaying the formed radiation source distribution image, the image of the examinee 28, or the like, and with a keyboard 94 for instructing the image processing unit 20 to operate. A mouse may be also connected, if necessary.

Figure 5:
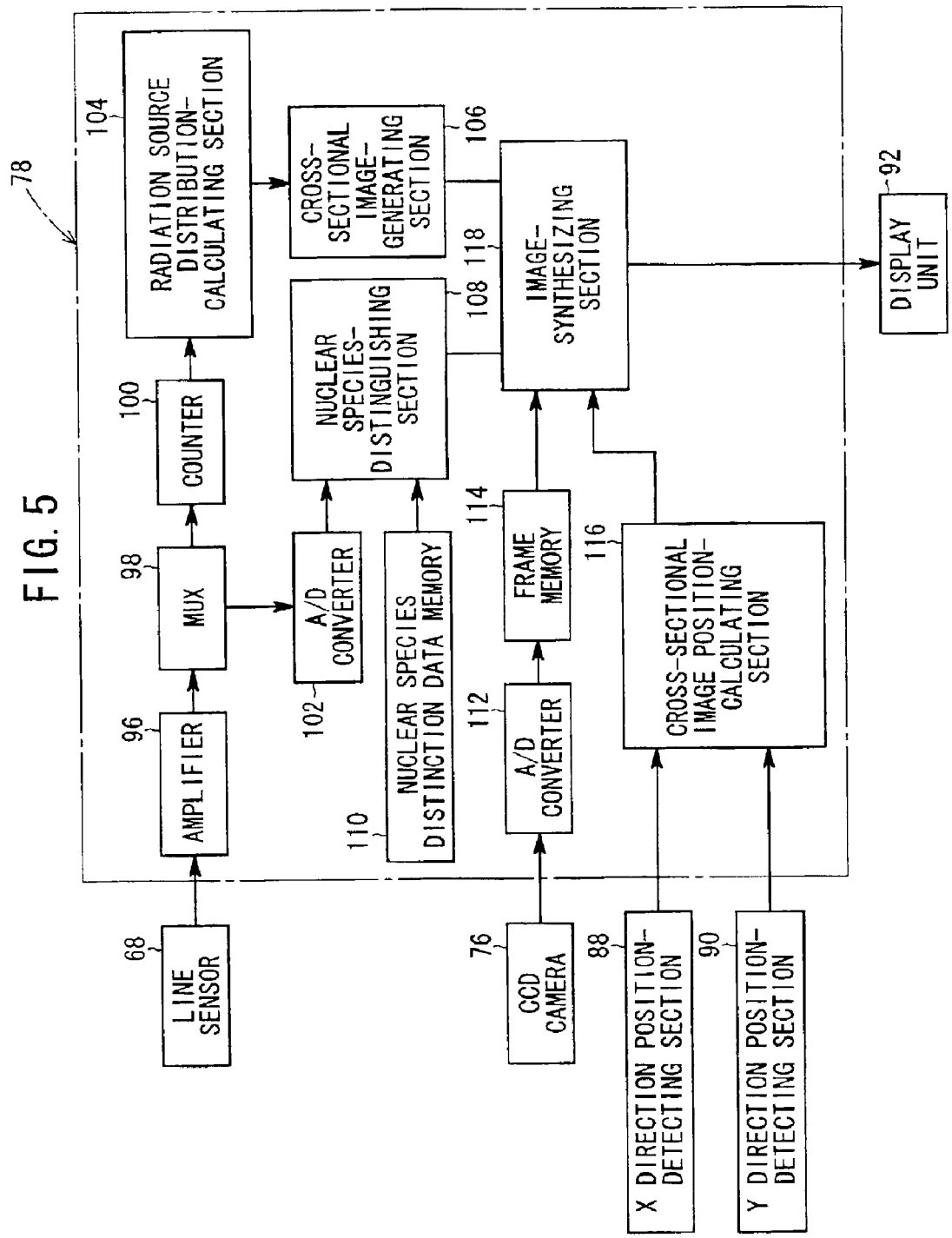
FIG. 5 shows a circuit block diagram of a signal processing circuit shown in FIG. 4.

FIG. 5 shows a circuit block diagram of the signal processing circuit 78 included in the image processing unit 20.

The respective semiconductor detection elements 66 of the line sensor 68 are connected to a multiplexer (MUX) 98 via an amplifier 96. The multiplexer 98 successively switches the radiation detection signals detected by the semiconductor detection elements 66 so that the signals are supplied to a counter 100. Further, the multiplexer 98 supplies the radiation detection signal to an A/D (analog/digital) converter 102.

The counter 100 counts the radiation based on the radiation detection signal, and the result is supplied to a radiation source distribution-calculating section 104. The radiation source distribution-calculating section 104 calculates the distribution of the radiation sources in the examinee 28 based on the number of counts of the radiation detected by the respective semiconductor detection elements 66. A cross-sectional image-generating section 106 generates a cross-sectional image of the examinee 28 of the radiation source distribution determined by the radiation source distribution-calculating section 104.

The A/D converter 102 converts the radiation detection signal into a digital signal which is supplied to a nuclear species-distinguishing section 108. The nuclear species-distinguishing section 108 compares the radiation detection signal supplied from the A/D converter 102 with the nuclear species distinction data as the radiation intensity data inherent in the nuclear species of the radiation sources supplied from a nuclear species distinction data memory 110 to specify the nuclear species of the radiation sources.

On the other hand, the CCD camera 76 is connected to an A/D converter 112. The two-dimensional image signal of the examinee 28 is converted into a digital signal by the A/D converter 112, and is stored in a frame memory 114. Further, the X direction position-detecting section 88 and the Y direction position-detecting section 90 are connected to a cross-sectional image position-calculating section 116. The cross-sectional image position-calculating section 116 calculates the cross-sectional position of the radiation source distribution detected by the detection unit 64 with respect to the examinee 28.

The cross-sectional image-generating section 106, the nuclear species-distinguishing section 108, the frame memory 114, and the cross-sectional image position-calculating section 116 are connected to an image-synthesizing section 118 (image-synthesizing means). The image-synthesizing section 118 synthesizes a desired image to be supplied to the display unit 92, based on the distribution image information of the radiation sources supplied from the cross-sectional image-generating section 106, the nuclear species information supplied from the nuclear species-distinguishing section 108, the image information of the examinee 28 supplied from the frame memory 114, and the cross-sectional position information supplied from the cross-sectional image position-calculating section 116.

The apparatus 10 for forming a radiation source distribution image according to the embodiment of the present invention is basically constituted as described above. Next, its operation, function, and effect will be explained.

The examinee 28 subjected to the inhalation of the radiation sources due to exposure to radiation, the examinee 28 subjected to radiation treatment, or the examinee 28 administered with radioisotope (RI) for detecting an affected part is placed on the stretcher 26 in a predetermined position between the guide rails 16a, 16b.

Subsequently, the X direction movement motors 30a, 30b are driven based on the command supplied from the signal processing circuit 78 of the image processing unit 20. The radiation information-detecting unit 18 which has been accommodated, for example, in the wall of a clinical laboratory is moved in one of the directions of the arrow X. That is, when the X direction movement motors 30a, 30b are driven, the wheels 34a to 34d connected by the chains 32a to 32d are rotated and the radiation information-detecting unit 18 is moved in one of the directions of the arrow X along the guide rails 16a, 16b.

While the radiation information-detecting unit 18 is moved in one of the directions of the arrow X, the detection unit 64 of the main body 24 is set such that the direction of array of the semiconductor detection elements 66 of the line sensor 68 is parallel to the directions of the arrow Y as shown in FIGS. 1 and 2. The detection unit 64 is moved along the examinee 28, keeping this arrangement. While the detection unit 64 is moved, the distance sensor 74 of the main body 24 detects the distance between the examinee 28 and the detection unit 64 to control the upward and downward movement of the detection unit 64 in the directions of the arrow Z so that the distance is constant. That is, the signal processing circuit 78 drives the Z direction movement motor 54 based on the distance signal detected by the distance sensor 74 to elevate or lower the detection unit 64 by the pinion 56 and the rack 50. Accordingly, the distance between the examinee 28 and the detection unit 64 is kept constant.

Then, the respective semiconductor detection elements 66 of the detection unit 64 detect the radiation from the radiation sources in the examinee 28 via the apertures 70 of the collimator 72. The radiation detected by the semiconductor detection elements 66 is supplied to the signal processing circuit 78, and the radiation is subjected to the signal processing as described below. The radiation source distribution image on the Y-Z tomographic plane of the examinee 28 is generated accordingly.

Figure 6:
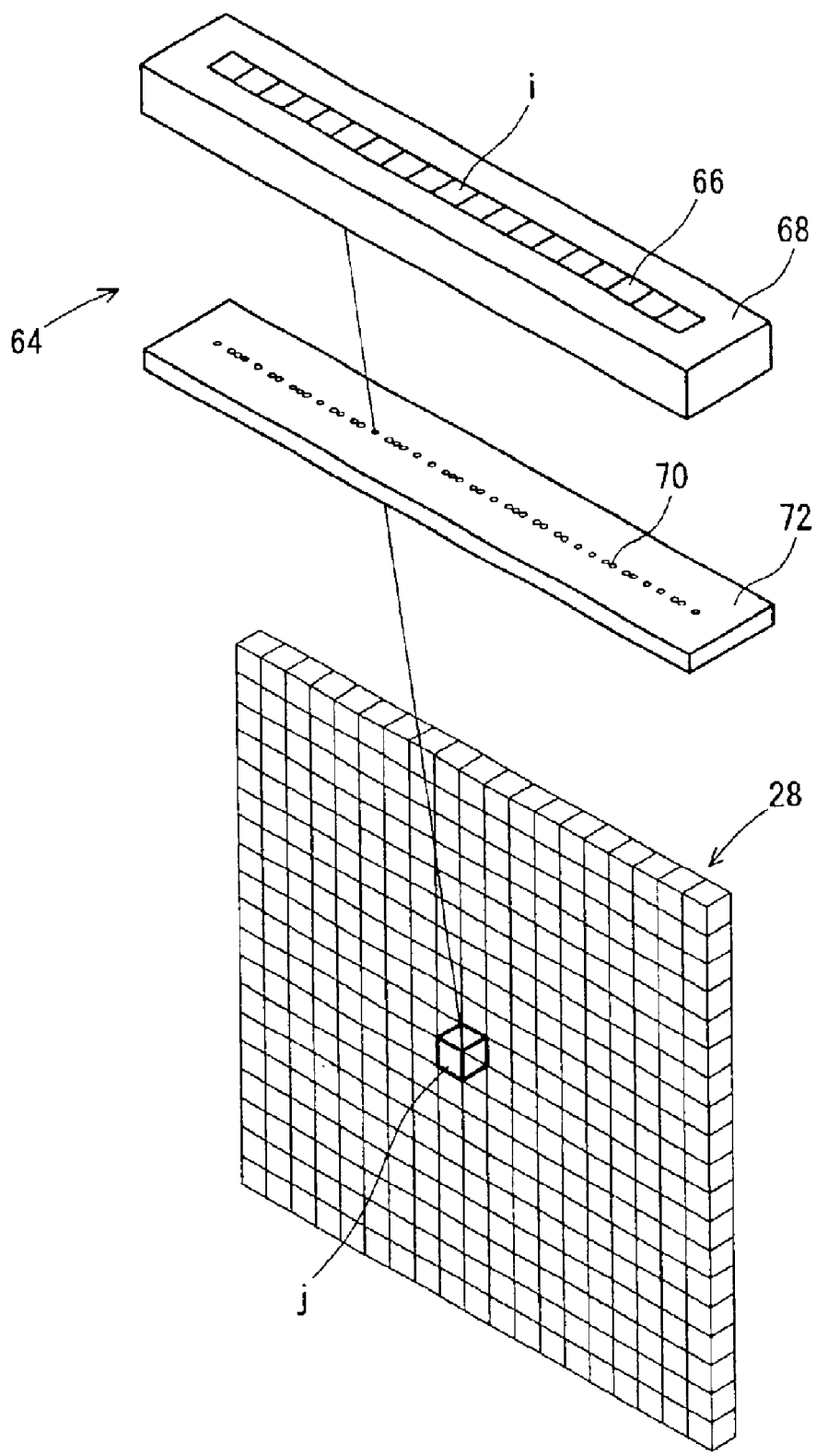
FIG. 6 illustrates the principle of the construction of a tomographic image with the apparatus for forming a radiation source distribution image according to the embodiment of the present invention.

A schematic view shown in FIG. 6 is depicted assuming that the examinee 28 is divided into n voxels on an arbitrary tomographic plane, one of the voxels is designated as j (j=1, 2, . . . , n), the number of elements of the semiconductor detection elements 66 for detecting the radiation is represented by m, and one of the elements is designated as i (i=1, 2, . . . , m).

It is assumed that $S_j$ represents the expected value of the number of counts of the radiation radiated by the j-th voxel for a certain period of time, $P_i$ represents the expected value of the number of counts of the radiation detected by the i-th semiconductor detection element 66 for the certain period of time, and $P^*_i$ represents the number of counts of the radiation actually detected. Assuming that $f_{ij}$ represents the probability of the detection of the radiation radiated from the j-th voxel by the i-th semiconductor detection element 66, the following expression is satisfied.

$$P_i = \sum_{j=1}^{n} f_{ij} S_j \qquad (i = 1, 2, \ldots, m) \tag{1}$$

The number of counts of the radiation from the radiation sources is randomly varied in accordance with the Poisson's distribution. Therefore, the number of counts detected by the i-th semiconductor detection element 66 is also randomly varied, and the expected value thereof $P_i$ is given by the expression (1).

The probability $f_{ij}$ is geometrically determined by the positional relationship among the j-th voxel, the i-th semiconductor detection element 66, and the aperture 70 of the collimator 72 and the M-sequence as an array pattern of the apertures 70. However, even under the ideal condition in which there is no absorption or scattering of the radiation, it is difficult to strictly determine the value of the probability $f_{ij}$ by calculation, because calculation amount is large. Therefore, in the actual calculation, the probability $f_{ij}$ is approximately determined assuming that the radiation source distribution in the voxel is represented by a dot radiation source placed at the center of the voxel.

That is, it is assumed that the route of the radiation radiated from the j-th voxel to arrive at the i-th semiconductor detection element 66 constitutes a cone having an apex at the center of the j-th voxel and having the bottom surface on the i-th semiconductor detection element 66, in which $\Omega$ represents a solid angle of the apex of the cone, and $\tau$ represents a ratio (transmittance in geometrical optics) of the area of the aperture 70 with respect to the area on the collimator 72 cut by the cone. On this assumption, the probability $f_{ij}$ is given as follows.

$$f_{ij} = (\Omega/4\pi) \cdot \tau \tag{2}$$

If the semiconductor detection element 66 is small as compared with the voxel, the cone can be constituted such that an apex is at the center of the semiconductor detection element 66 and the bottom surface is on one plane of the voxel. Accordingly, it is possible to determine the probability $f_{ij}$ from the cone more highly accurately.

It is assumed that the distribution of the radiation sources is represented by $S=(S_1, S_2, \ldots, S_n)$, and the number of counts of the radiation is represented by $P^*=(P^*_1, P^*_2, \ldots, P^*_m)$. On this assumption, the conditional probability (likelihood) $\text{Prob}(P^*|S)$, with which the number of counts $P^*$ is obtained under the condition that the distribution S is observed, is represented by the following expression (3) by using the expression of the Poisson's distribution and the expression (1). In the expression (3), the symbol "^" represents power or exponentiation.

$$\text{Prob}(P* \mid S) = \prod_{i=1}^{m} (P_i\hat{\,} P*_i / P*_i\,!) \cdot \exp(-P_i) \tag{3}$$

In the signal processing circuit 78, the distribution S of the radiation sources in which the conditional probability Prob($P^*|S$) in the expression (3) is maximum is determined asymptotically.

Figure 7:
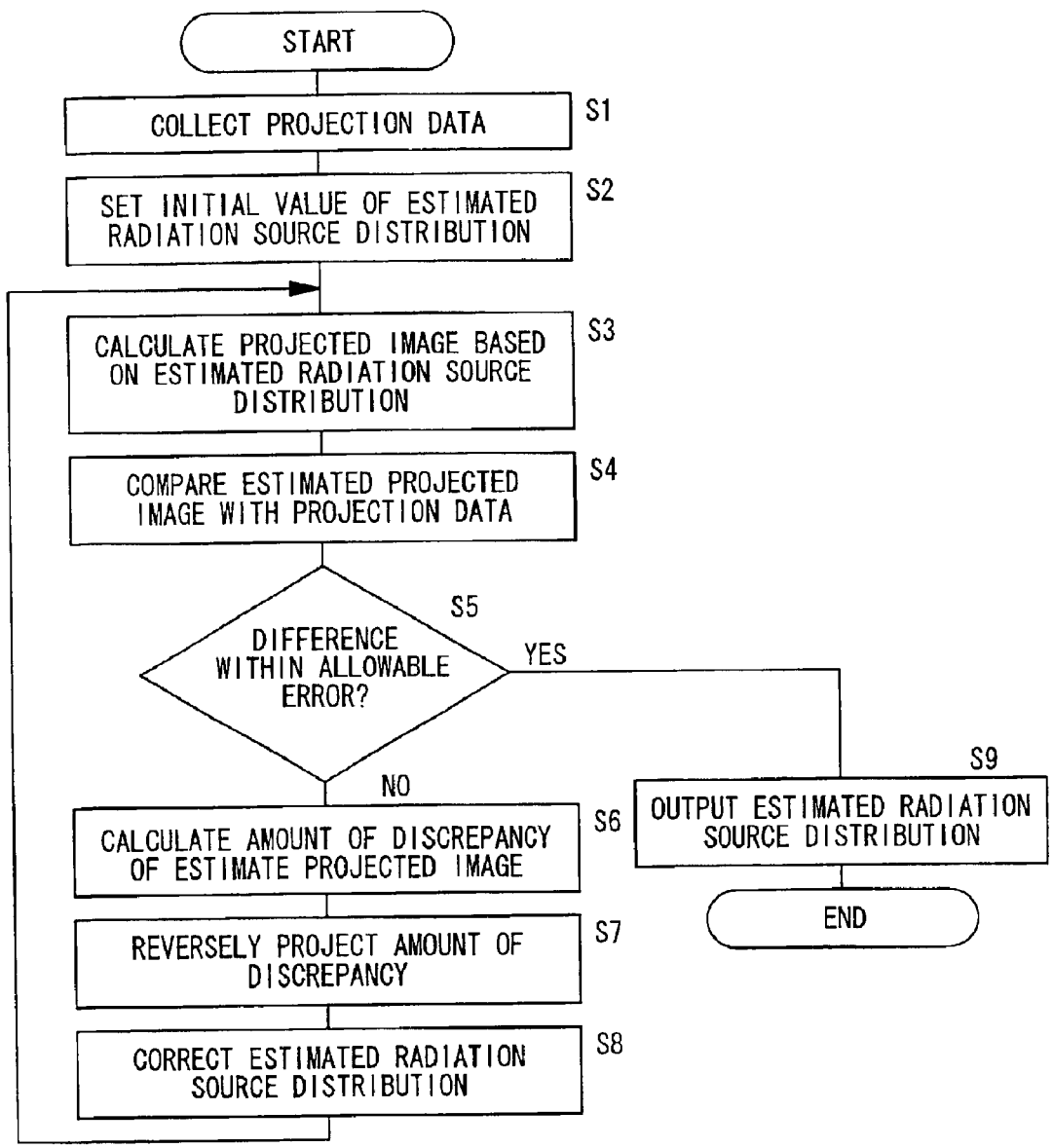
FIG. 7 shows a process flow chart illustrating the construction of the tomographic image with the apparatus for forming a radiation source distribution image according to the embodiment of the present invention.

FIG. 7 shows a flow chart illustrating the process for specifically determining the radiation source distribution S by using the expression (3) in the signal processing circuit 78 shown in FIG. 5.

At first, the radiation from the radiation sources in the examinee 28 is detected by the semiconductor detection elements 66 through the collimator 72. The result is sent via the amplifier 96 and the multiplexer 98 into the counter 100 for counting the radiation. The radiation source distribution-calculating section 104 incorporates the count signal from the counter 100 to collect the number of counts $P^*$ as the projection data of the radiation sources (Step S1). Subsequently, the initial value of the estimated radiation source distribution S is set (Step S2), and then the expected values $P=(P_1, P_2, \ldots, P_m)$, which represent the estimated projected image of the radiation sources, are calculated (Step S3). The initial values of the estimated radiation source distribution S may be values distributing uniformly, for example.

Subsequently, the expected values P, which represent the estimated projected image determined in Step S3, are compared with each number of counts $P^*$ which is the projection data collected in Step S1 (Step S4) to judge whether or not differences are within an allowable error (Step S5). If the differences are not within the allowable error, each amount of discrepancy $P^*/P$ of the estimated projected image is calculated (Step S6). Each amount of discrepancy $P^*/P$ is reversely projected onto the examinee 28 (Step S7) to correct the estimated radiation source distribution S (Step S8).

Each of the expected values P asymptotically approaches each number of counts $P^*$ by repeatedly performing the processes of Steps S3 to S8. If it is judged in Step S5 that the differences between the expected values P and the numbers of counts $P^*$ are within the allowable error, the estimated radiation source distribution S is supplied to the cross-sectional image-generating section 106 (Step S9) as the radiation source distribution image data on the Y-Z tomographic plane of the examinee 28.

On the other hand, the main body 24 of the radiation information-detecting unit 18 has the CCD camera 76 separating at a constant distance from the detection unit 64 in the directions of the arrow X. Two-dimensional image data of the examinee 28 photographed by the CCD camera 76 is converted into the digital data by the A/D converter 112, and then the data is once stored in the frame memory 114. The cross-sectional image position-calculating section 116 determines the position (X direction position data) of the Y-Z tomographic plane of the radiation source distribution image data in the directions of the arrow X, by using the detection signal supplied from the X direction-position-detecting section 88 installed to the X direction movement motor 30a, 30b.

Subsequently, the image-synthesizing section 118 combines the radiation source distribution image data on the Y-Z tomographic plane of the examinee 28 generated by the cross-sectional image-generating section 106 with the two-dimensional image data of the examinee 28 stored in the frame memory 114. When the images are combined, the image-synthesizing section 118 cuts out the two-dimensional image data from the frame memory 114, based on the X direction position data of the radiation source distribution image data supplied from the cross-sectional image position-calculating section 116, and the two-dimensional image data is combined with the radiation source distribution image data to be displayed on the display unit 92.

Figure 8:
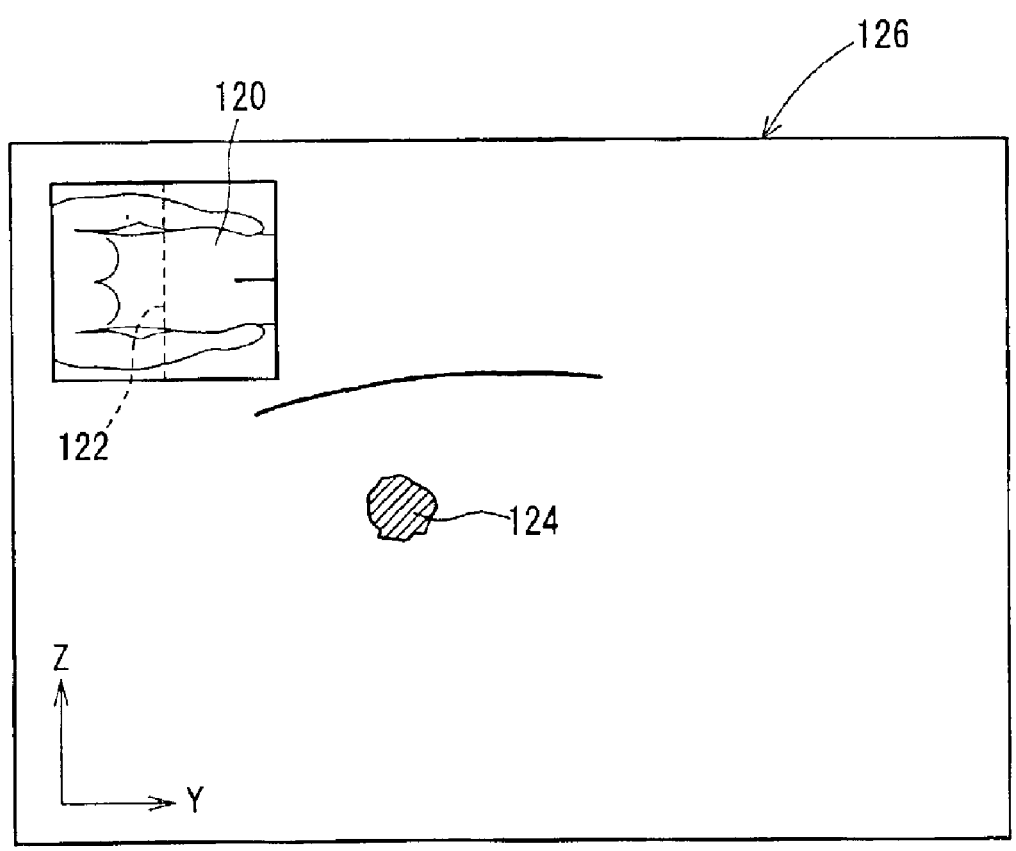
FIG. 8 illustrates a synthetic image prepared by the apparatus for forming a radiation source distribution image according to the embodiment of the present invention.

FIG. 8 illustrates a synthetic image 126 combining a photographed image 120 of the examinee 28 with a radiation source distribution image 124 on the Y-Z tomographic plane indicated by a cursor 122 on the photographed image 120.

The apparatus 10 for forming a radiation source distribution image displays the synthetic image 126 as described above. Accordingly, it is possible to confirm the position of the radiation source distribution image 124 since the photographed part can be easily specified with the photographed image 120.

When the distribution area of the radiation sources is desired to be roughly confirmed, the radiation information-detecting unit 18 may be moved at a high speed in one of the directions of the arrow X and roughly generate radiation source distribution images 124, by the radiation source distribution-calculating section 104 and the cross-sectional image-generating section 106.

When the collimator 72 is detached from the detection unit 64 to directly incorporate the radiation information by using the line sensor 68, then it is possible to mitigate calculation load on the radiation source distribution-calculating section 104, and it is possible to quickly specify the location of the radiation sources. That is, no calculation is performed in the radiation source distribution-calculating section 104 of the signal processing circuit 78, and the location of the radiation sources in the examinee 28 can be directly specified from the number of radiation counted by the counter 100.

After the location of the radiation sources is confirmed without the collimator 72, the collimator 72 is installed to the line sensor 68 to perform the scanning at a low speed by the radiation information-detecting unit 18 in one of the directions of the arrow X in the vicinity of the confirmed location. Accordingly, it is possible to obtain the detailed radiation source distribution image 124. In this procedure, the resolution of the radiation source distribution image 124 in the directions of the arrow Y is determined by the number of elements of the semiconductor detection elements 66. However, the resolution in the directions of the arrow X can be arbitrarily adjusted depending on the movement speed of the radiation information-detecting unit 18 in the directions of the arrow X.

With the radiation information-detecting unit 18, the radiation source distribution image 124 on an Y-Z tomographic plane is obtained as described above. After that, if necessary, it is possible to form a radiation source distribution image on an X-Z tomographic plane.

When the distribution area of the radiation sources is confirmed by moving the radiation information-detecting unit 18 in the directions of the arrow X, and the radiation information-detecting unit 18 is stopped over the distribution area. Subsequently, the revolution motor 58 is driven to revolve the detection unit 64 by 90° by the gear 60. During this process, the distance sensor 74 and the CCD camera 76, which are connected to the disk 73, are also revolved by 90°.

Subsequently, the Y direction movement motor 42 is driven to move the detection unit 64 in the directions of the arrow Y by the pinion 44 and the rack 38. The radiation information is obtained while the distance between the examinee 28 and the detection unit 64 is kept constant by the using the distance sensor 74.

Figure 9:
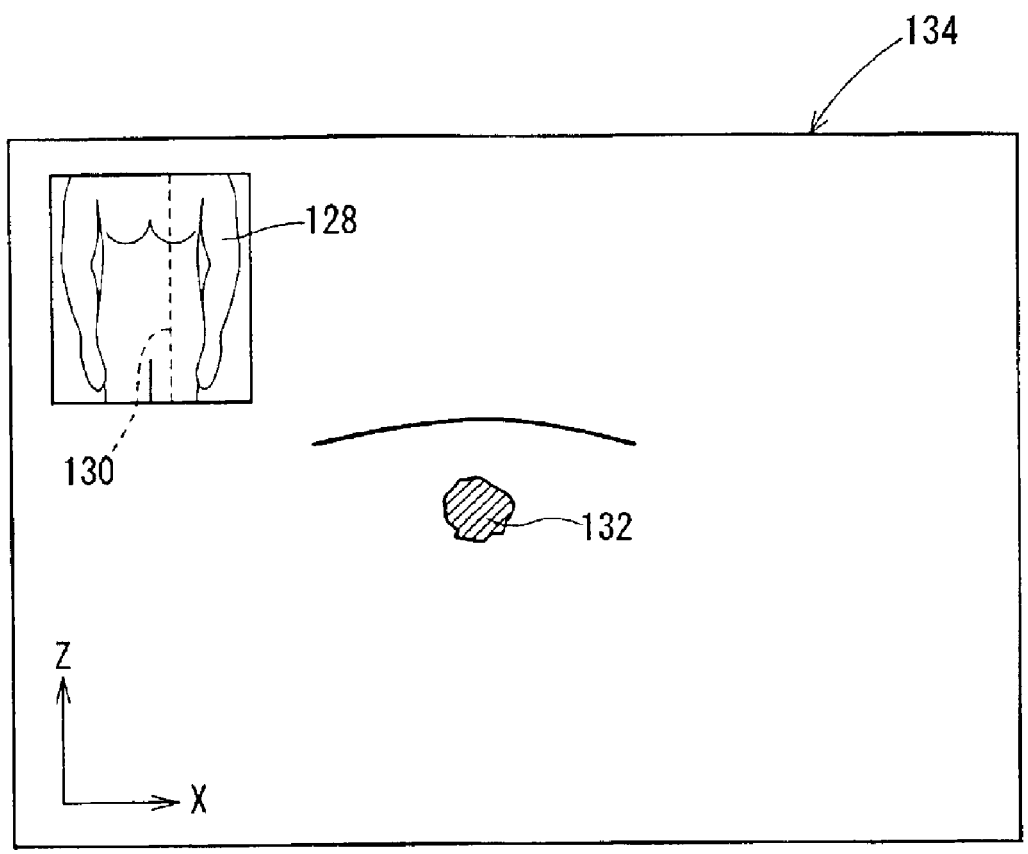
FIG. 9 illustrates a synthetic image prepared by the apparatus for forming a radiation source distribution image according to the embodiment of the present invention.

FIG. 9 illustrates a synthetic image 134 obtained by combining an image 128 photographed by the CCD camera 76 with a radiation source distribution image 132 of the examinee 28 on an X-Z tomographic plane specified by a cursor 130 on the photographed image 128. The position of the cursor 130 can be determined based on the position (Y direction position data) of the detection unit 64 in the directions of the arrow Y detected by the Y direction position-detecting section 90.

The radiation source distribution image 132 on the X-Z tomographic plane can be adjusted to have an arbitrary resolution by changing the movement speed of the detection unit 64 in the directions of the arrow Y.

The intensity of the radiation differs depending on nuclear species. In the apparatus 10 for forming a radiation source distribution-image according to the embodiment of the present invention, the nuclear species of the radiation sources can be distinguished by using the detected intensity.

In the signal processing circuit 78, detection signals of the radiation detected by the semiconductor detection elements 66 are amplified by the amplifier 96 and sent to the multiplexer 98, and then the signals are converted into the detection data as the digital signal by the A/D converter 102. In the nuclear species-distinguishing section 108, the detection data is compared with the nuclear species distinction data stored in the nuclear species distinction data memory 110 to specify the nuclear species of the radiation sources. The specified nuclear species data is supplied to the image-synthesizing section 118 to be displayed on the display unit 92 together with the synthetic image 126. Then, it is possible to perform a more appropriate treatment for the examinee 28.

The embodiment described above has been explained assuming that the radiation source distribution image is formed for the X-Z tomographic plane or the Y-Z tomographic plane of the examinee 28. However, it is also possible to form a radiation source distribution image on an X-Y tomographic plane of the examinee 28 or a three-dimensional radiation source distribution image by using the radiation source distribution images described above.

Figure 10:
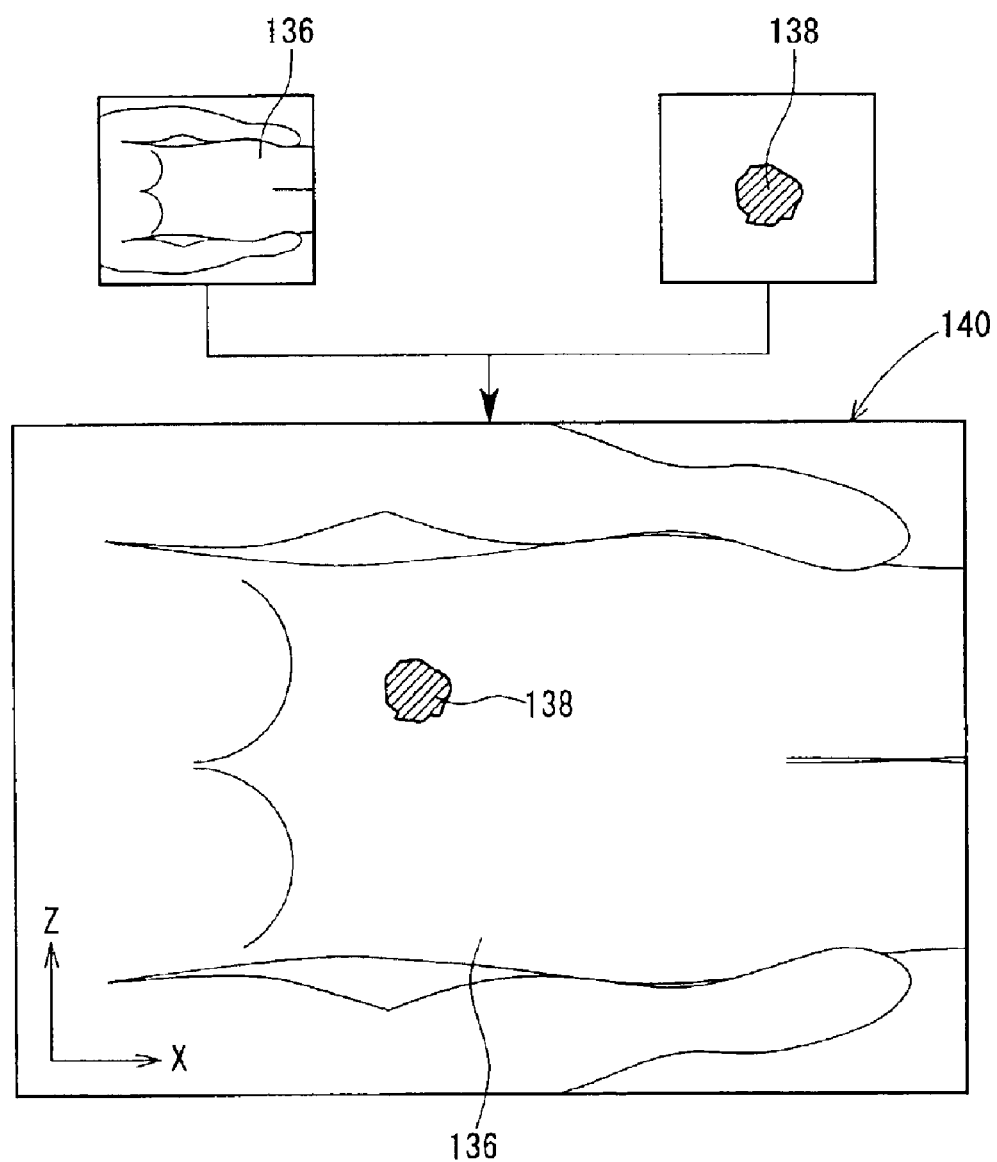
FIG. 10 illustrates a synthetic image prepared by the apparatus for forming a radiation source distribution image according to the embodiment of the present invention.

FIG. 10 illustrates a synthetic image 140 obtained by combining an image 136 of the examinee 28 photographed by the CCD camera 76 and a radiation source distribution image 138 on the X-Y tomographic plane formed based on the radiation detected by the semiconductor detection elements 66.

After the synthetic images 126, 134, 140 of the examinee 28 are obtained and the predetermined diagnosis treatment is completed, the radiation information-detecting unit 18 is moved along the guide rails 16a, 16b, and thus the radiation information-detecting unit 18 is accommodated, for example, in the wall of a clinical laboratory. Therefore, the space in the clinical laboratory can be effectively used without being obstructed by the apparatus 10. Further the transportable stretcher 26 can be used for the apparatus 10 for forming a radiation source distribution image, which is advantageous since it is unnecessary to provide any dedicated cot for photographing.

What is claimed is:

1. An apparatus for forming a radiation source distribution image for detecting radiation radiated from a radiation source in an examinee to form a distribution image of said radiation source in said examinee, said apparatus comprising:

a line sensor including a plurality of radiation-detecting elements for detecting said radiation, said plurality of radiation-detecting elements being arranged one dimensionally;

a coded aperture plate arranged between said line sensor and said examinee, including a plurality of apertures arranged one dimensionally according to a predetermined array rule in a same direction as said radiation-detecting elements;

a movable means for moving said line sensor and said coded aperture plate in unison in a direction perpendicular to the direction in which said radiation-detecting elements and said apertures are arranged;

an image-forming means for forming said distribution image of said radiation source based on said radiation detected by said radiation-detecting elements; and a display means for displaying said distribution image of said radiation source formed by said image-forming means.

2. The apparatus according to claim 1, wherein said coded aperture plate includes said plurality of apertures arranged one dimensionally according to an array rule of M-sequence.

3. The apparatus according to claim 1, wherein said coded aperture plate is detachable from said line sensor.

4. The apparatus according to claim 1, wherein said movable means includes a first movement mechanism for moving said line sensor in a first direction along said examinee, a second movement mechanism for moving said line sensor in a second direction perpendicular to said first direction along said examinee, and a revolution mechanism for revolving said line sensor so that said direction of said plurality of radiation-detecting elements is perpendicular to said first direction or said second direction.

5. The apparatus according to claim 1, further comprising an elevating/lowering mechanism for adjusting a distance between said line sensor and said examinee.

6. The apparatus according to claim 5, further comprising a distance sensor for detecting said distance between said line sensor and said examines.

7. The apparatus according to claim 1, wherein each of said radiation-detecting elements is a semiconductor detection element of CdTe or CdZnTe.

8. The apparatus according to claim 1, further comprising a photographing unit for photographing a two dimensional image of said examinee, wherein said display means displays said distribution image of said radiation source and said two dimensional image of said examinee.

9. The apparatus according to claim 8, further comprising an image-synthesizing means for superimposing said distribution image of said radiation source on said two dimensional image of said examinee.

10. The apparatus according to claim 1, further comprising:

memory means for memorizing nuclear species distinction data, said data including radiation intensity data inherent in nuclear species; and nuclear species-specifying means for specifying a nuclear species of said radiation by comparing intensity data of said radiation detected by said line sensor with said radiation intensity data inherent in nuclear species.

11. The apparatus according to claim 1, wherein said radiation source is a radioisotope administered to said examinee.

* * * * *